United States Patent

Tu

[19]

[11] Patent Number: 6,165,206
[45] Date of Patent: Dec. 26, 2000

[54] APPARATUS FOR MEDICAL ABLATION USE AND METHODS THEREOF

[76] Inventor: Hosheng Tu, 2151 Palermo, Tustin, Calif. 92782

[21] Appl. No.: 09/313,429

[22] Filed: May 17, 1999

Related U.S. Application Data

[62] Division of application No. 09/036,380, Mar. 6, 1998, Pat. No. 5,948,009.

[51] Int. Cl.[7] ....................................................... A61F 7/00
[52] U.S. Cl. ............................ 607/96; 607/102; 606/169; 604/20
[58] Field of Search ...................... 607/96–102; 606/159, 606/169; 601/15, 17, 21, 1; 600/439; 604/20

[56] References Cited

U.S. PATENT DOCUMENTS 4,936,281  6/1990  Statz .
5,176,677  1/1993  Wuchinich ................................. 606/46

*Primary Examiner*—Linda C. M. Dvorak
*Assistant Examiner*—Roy Gibson

[57] ABSTRACT

An ablation device and methods thereof for treating canker sores or reducing the mass of cellular tissue, wherein an elongated tubular element comprises at least one electrode disposed at its distal section, RF energy generating means, and means for generating vibration at the distal section of the tubular element to effect the ablation and the vibrational massage therapy for the tissue.

8 Claims, 4 Drawing Sheets

APPARATUS FOR MEDICAL ABLATION USE AND METHODS THEREOF

CROSS-REFERENCE TO RELATED APPLICATIONS

This is a division of application Ser. No. 09/036,380, filed on Mar. 6, 1998, now U.S. Pat. No. 5,948,009 allowed.

TECHNICAL FIELD OF THE INVENTION

The present invention generally relates to an improved apparatus and methods, for medical purposes, of creating lesions and, more particularly, to such an apparatus and methods for treating the canker sores and/or tissues in a patient by delivering RF energy to the lesion sites with vibrational massage therapy.

BACKGROUND OF THE INVENTION

Destruction of cellular tissues in situ has been used in the treatment of many diseases or as an adjunct to surgical removal procedures. It is often less traumatic than surgical procedures and may be the only alternative, wherein other procedures are unsafe. Ablative treatment devices have an advantage of using a destructive energy that is rapidly dissipated and reduced to a non-destructive level by conduction and convection, to forces of circulating fluids and other natural processes.

Devices using microwave energy, radiofrequency energy, ultrasonic energy, cryogenic, laser energy, and tissue destructive substances have been used to destroy malignant, benign, and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radiofrequency electrode or microwave energy antenna, through a duct, to the zone of treatment, and applying energy diffusively through the duct wall into the surrounding tissue in the targeted directions.

Canker sores are also known as aphthous ulcerations, or recurrent aphthae, which are painful sores usually formed in the mucus membrane of the mouth. The sores first appear as small red lesions that quickly whiten and then break down to form shallow ulcers. Many people, especially small children with less immunity to ulcerations, experience the pain and discomfort of canker sores for a period from several days to a couple of weeks. While the cause of canker sores has not been identified, several pharmaceutical approaches have been taken. However, they only coat the surface of the canker sore by a relieving agent, and mask the problem for temporary relief of pain and stress.

Price, Jr. in U.S. Pat No. 5,686,095, Alliger in U.S. Pat. No. 5,516,799, Marcus et al. in U.S. Pat. No. 5,182,104, Leeds in U.S. Pat. No. 4,466,956, and Hodosh in U.S. Pat. No. 4,191,750 all teach a topical treatment for canker sores. However, none of above-mentioned patents discloses the method for treating canker sores by heat, using a RF energy source with the assistance of the vibrational massage therapy.

Of particular interest to the present invention are RF therapeutic protocols, which have been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after locating the sore sites for treatment. Radiofrequency energy, when coupled with a temperature control mechanism, can supply precise energy to the device-to-tissue contact site to obtain the desired temperature for creating a lesion.

To be more efficient in RF energy ablation, the electrode with a vibration capability shall be used to simultaneously deliver the massage therapy to the target tissue. The electric toothbrush with vibration has been disclosed in the following patents: Suyama in U.S. Pat. No. 4,944,296, Ng in U.S. Pat. No. 5,283,921, Hwang in U.S. Pat. No. 5,381,576, Okada in U.S. Pat No. 5,421,726, Mei in U.S. Pat. No. 5,617,603, and Hahn in U.S. Pat. No. 5,651,157. All the above patents disclose the advantage of an electric toothbrush with vibration. However, they are short of using an ablation electrode with vibration capability to create a lesion in the tissue for therapeutic purpose.

On the other hand, Imran in U.S. Pat. No. 5,281,218 entitled "Catheter having needle electrode for radiofrequency ablation" teaches a method using a needle electrode that is attached onto a catheter for radiofrequency ablation. Though a needle-like electrode is beneficial to ablate a tissue point for deep lesion, it is not disclosed that the particular needle electrode could possibly combine massage therapy for proper contact with the target tissue.

Edwards et al. in U.S. Pat. No. 5,456,662 entitled "Method for reducing snoring by RF ablation of the uvula" teaches a medical ablation method for reducing snoring wherein a flexible RF electrode wire is inserted into the uvula and RF energy is applied to the uvula tissue to cause internal lesions. Edwards et al. does not disclose a catheter to ablate tissue, having the capability for simultaneously delivering radiofrequency energy and vibrational massage therapy.

Therefore, there is a need for an improved apparatus and methods using the radiofrequency energy to treat canker sores or tumors, while applying vibrational massage therapy.

SUMMARY OF THE INVENTION

In general, it is an objective of the present invention to provide a method and an improved medical device for generating heat, to treat canker sores or cellular tissue. It is another objective of the present invention to provide an apparatus so that vibrational massage therapy can be applied to the canker sore site, or the targeted cellular tissue, for intimate contact. It is another objective of the present invention to provide a method and a device for monitoring the temperature of the medical device, and to control the temperature by utilizing a temperature control mechanism and/or algorithm. The location of the temperature sensor means is preferably at the proximity of the tip of the medical device. It is still another objective of this invention to provide a method and a device for treating canker sores or cellular tissue in a patient by delivering a therapeutic agent to the lesion sites.

Briefly, heat is generated by applying a suitable energy source to a device, which comprises an electrode means, in contact with the body tissue. A suitable energy source may consist of radiofrequency energy, microwave energy, ultrasonic energy, alternating current energy, or laser energy. The energy can be applied to the canker sore or cellular tissue through the electrode means. A DIP (dispersive indifferent pad) type pad, that contacts the patient, is connected to the Indifferent Electrode Connector on the RF generator. When using an alternating current outlet, the generator should be grounded to avoid electrical interference. Heat is controlled by the power of the RF energy delivered and by the delivery duration. The standard RF energy generator means and its applications through the electrode means, to a patient are well known for those who are skilled in the art.

In a further embodiment, means for generating vibration at the distal section comprises a motor mounted in the cavity of the handle, which has a rotatable motor shaft, an elongated connecting shaft having a first end, to which the electrode is connected, and a second end connected to the handle, a weight eccentrically mounted on the motor shaft with respect to the motor shaft axis, so as to rotate eccentrically, so that when the motor shaft rotates, the electrode vibrates.

In one embodiment, the device is leak-proof so that the therapeutic agent, in either fluid phase or gel phase, can be forced under a positive pressure to flow inside the lumen of the medical device from its proximal end to the distal end. The fluid is vented through an opening at the proximity of the electrode to effect the therapeutic purpose.

The method and apparatus of the present invention has several significant advantages over other known systems or techniques to treat the canker sore. In particular, the device system comprising of the electrode means, using RF energy as a heat source, in this invention and simultaneously delivering vibrational massage therapy to the lesion sites, results in a more efficient therapeutic effect, which is highly desirable in its intended application on canker sores and on other medical ablation applications.

BRIEF DESCRIPTION OF THE DRAWINGS

Additional objectives and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Figure 1:
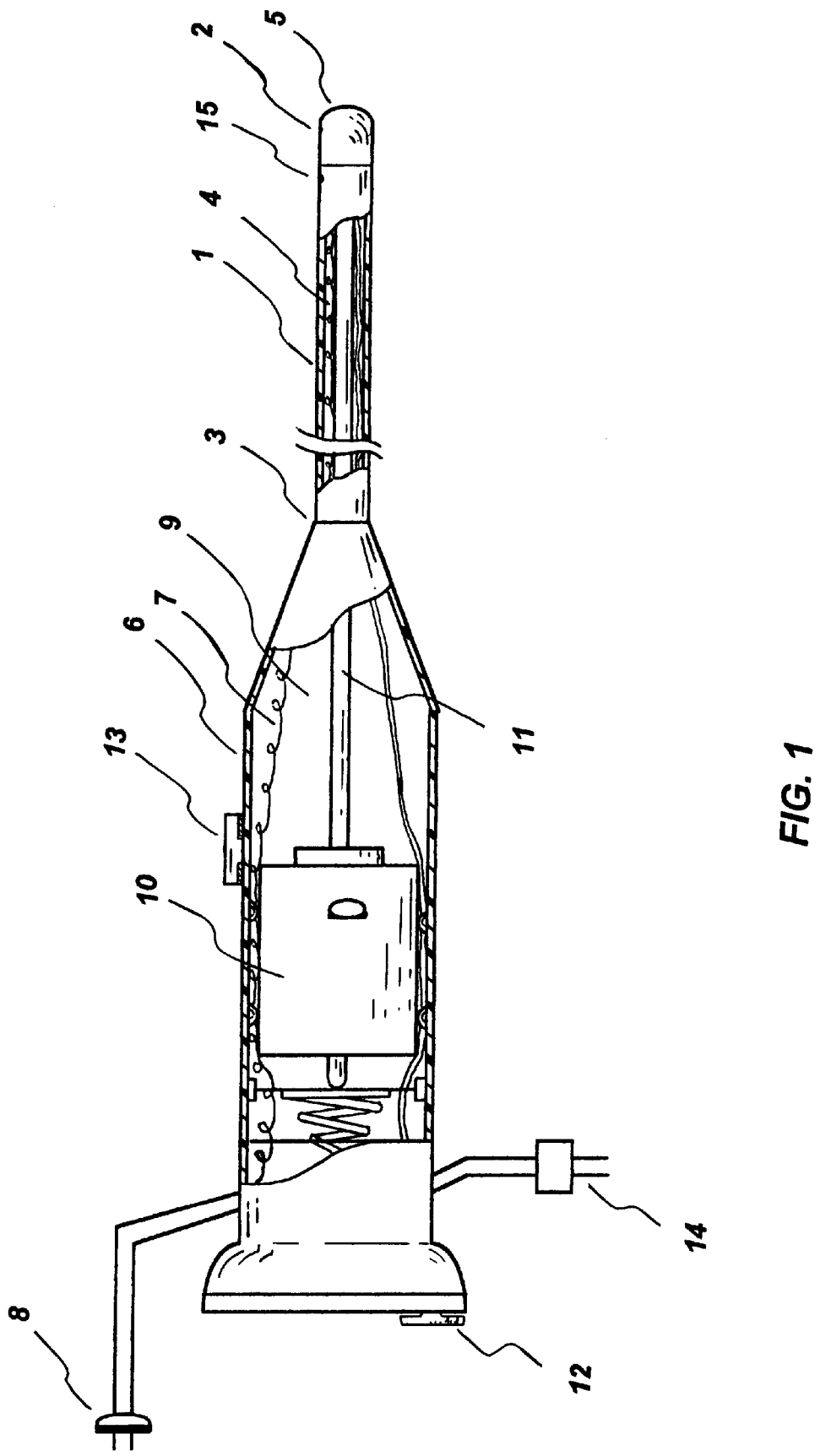
FIG. 1 is an over-all view of the ablation device, having an electrode means and an electric vibration means, constructed in accordance with the principles of the present invention.

Referring to FIGS. 1 to 4, what is shown is an embodiment of the ablation device system, by simultaneously applying radiofrequency energy and applying a vibrational therapeutic massage to treat the canker sore or cellular tissue of a patient. As shown in FIG. 1, the ablation device in the form of an elongated tubular element 1 comprises a distal section, a distal end 2, a proximal end 3, and at least one lumen 4 extending therebetween; wherein at least an electrode means 5 is disposed at the distal section, and wherein the electrode means 5 has a conductive surface for contacting the target tissue. The ablation device also comprises a handle 6 secured at the proximal end 3 of the tubular element 1, wherein the handle has a cavity 9; and means for supplying radiofrequency energy from an external RF energy generating means to the electrode means 5 of the ablation device system. A conducting wire 7, which is connected by connector 8 at the proximal end of the handle 6, is used to transmit the RF energy. The distal section of the ablation device is somewhat bendable. The RF energy supply is controlled by an on-off switch button 13 located conveniently on the handle 6.

There is a cavity 9 inside the handle 6, in which a motor 10 is located. The electrode means 5 is connected to the handle 6 by a shaft 11. In one embodiment, a battery means (not shown), which is located at the proximal end of the cavity 9 of the handle 6, is used to supply the energy to the motor 10. In an alternate embodiment, the motor 10 is powered by an alternate current (AC) through a power input plug (not shown). In either case, the power supply is controlled by an on-off switch button 12 located conveniently at the proximal end of the handle 6.

In another embodiment, a fluid infusion means 14 is provided for the irrigation of a desired therapeutic agent, in either fluid phase or gel phase, to the canker sore site or to the targeted cellular tissue site. The fluid is adapted to diffuse out of the device at an opening 15 at the proximity of the electrode means 5. Optionally, the distal portion of the device comprises a coil-like element so that the distal portion close to the distal end is manually bendable or steerable. The outer surface of the ablation device, except the electrode means at its distal end, is not conductive.

Figure 2:
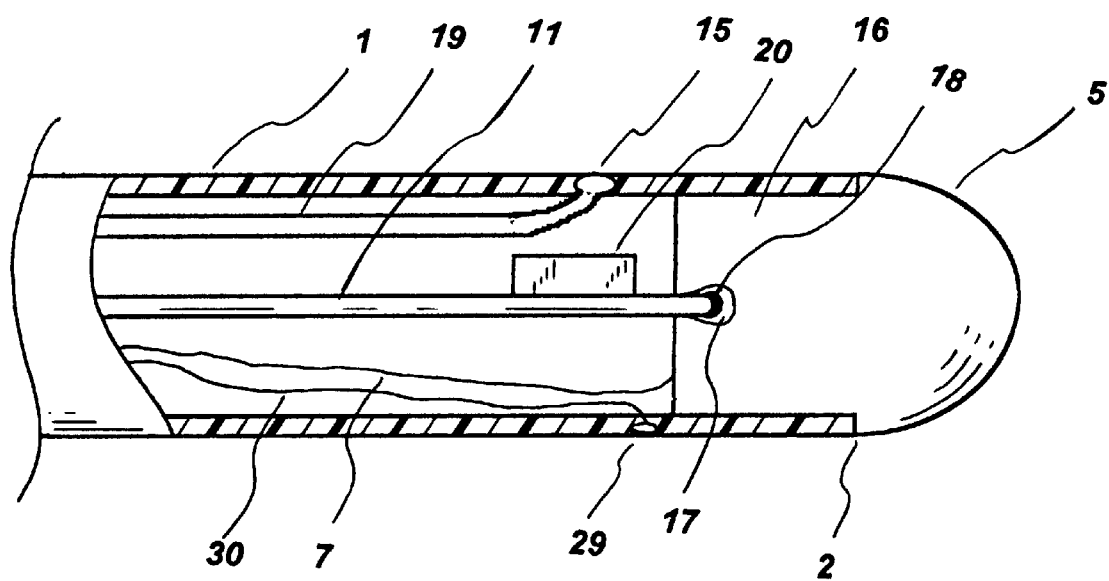
FIG. 2 is a cross-sectional view of the distal portion of the ablation device in FIG. 1.

FIG. 2 is a cross-sectional view of the distal portion of the ablation device. The elongated tubular element 1 comprises a tip electrode 5 at the distal end 2 of the tubular element 1, wherein the electrode has a stem 16, and a receptor hole 17 for loosely holding the distal end 18 of the shaft 11 inside the receptor hole 17. The shape of the distal end 18 is in the form of a ball-type end, so that the end 18 stays securely inside the hole 17, even at the vibration state. A RF energy conducting wire 7 is located within the lumen of the tubular element 1. One end of the conducting wire 7 is secured and connected to the electrode means 5 at the distal end 2 while the other end of the conducting wire is secured to a contact pin of the connector 8, wherefrom the conducting wire is connected to an external RF generator means (not shown).

Attached to the shaft 11 there is an eccentric weight 20. The eccentric rotation of the weight 20 places the tip electrode 5 into vibration via the shaft 11 due to the unbalancing effect of the eccentric weight 20. The vibrational amplitude of the tip electrode 5 of the tubular element 1 is determined by the geometry of the shaft 11, the mass and configuration of the weight 20, and the rotational speed of the motor 10, among other factors.

In one embodiment, a temperature sensing means 29 is disposed close to the electrode means 5. An insulated temperature sensor wire means 30 passes from the temperature sensing means 29 at the distal end, to an external temperature control mechanism through the outlet connector 8. The RF energy delivery is controlled by the measured temperature from the temperature sensing means 29, a closed-loop temperature control mechanism and/or algorithm. When the measured temperature rises to the preset high-limit point, the temperature control mechanism sends out a signal to cut off the RF energy supply. In a similar manner, when the measured temperature drops to the preset low-limit point, the temperature control mechanism sends out a signal to activate the RF energy supply.

In a further embodiment, a fluid infusion means is provided for irrigation of the therapeutic agent. The said therapeutic agent is selected from the group of heparin solution, saline solution, fluoroquinolone, lactic acid, glycolic acid, alpha hydroxy organic acids, vitamins, povidone-iodine, nitrate compounds, virucidal agents, anti-inflammatory agents, antibiotics and/or their mixtures. A conduit 19 is provided inside the lumen of the tubular element 1 for transporting the fluid or gel from the proximal end 3 of the tubular element 1 to the distal end 2. Thereafter the fluid or gel is diffused out the tubular element 1 through the opening 15.

Figure 3:
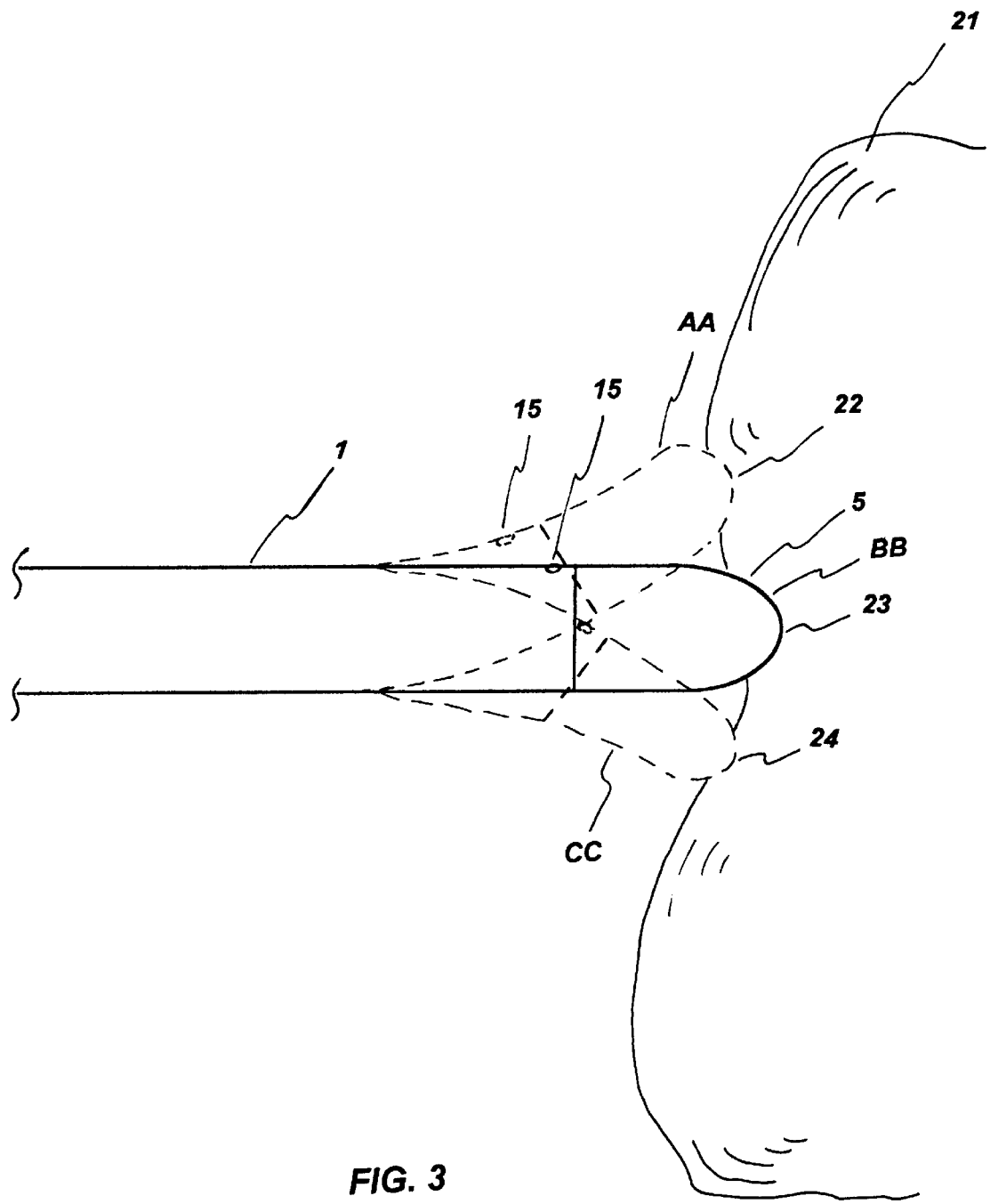
FIG. 3 shows a perspective view of a canker sore region being treated by the ablation device of the present invention.

FIG. 3 shows a perspective view of a canker sore region being treated by the ablation device of the present invention. The distal section of the tubular element 1 has the capability of vibration. The tip electrode 5 may contact the tissue 21 between the points 22 and 24 during its vibration state to effect the vibrational massage therapy. The distal end 2 of the tubular element 1 is correspondingly in any of the AA, BB or CC locations during the vibration state. The external RF energy generator means has the capability to supply RF energy by controlling the time, power, and temperature through an optional separate closed-loop temperature control means. The patient is connected to the RF generator means through a DIP electrode to form a closed-loop current system. Therefore, RF energy is applied and delivered to the target canker sore region, through the electrode means of this invention. The radiofrequency energy current in this invention is preferably within the range of 50 to 2,000 kHz. The frequency of the vibration of the ablation device in this invention is preferably within the range of 60 to 1000 cycles per minute. By simultaneously applying RF energy to the electrode and applying the vibrational massage therapy topically, the canker sore can be treated. During the RF ablation, therapeutic fluid, in liquid or gel form, may also be provided through the irrigation port 15 to the canker sore region.

The method for treating the canker sore of a patient comprises: (a) inserting an ablation device into the mouth of the patient, wherein the ablation device has a distal section, a distal end, a proximal end, a lumen extending therebetween, a handle, which has a cavity, attached at the proximal end of the device, and at least an opening at the distal section, wherein a tip electrode is disposed at the distal end, wherein the ablation device is leak-proof, except for the opening at the distal section, and wherein the ablation device comprises means for generating vibration at the distal section, which is located within the handle; (b) contacting the electrode of the device against the canker sore of the patient; (c) applying RF energy through a conducting wire to the tip electrode of the device to effect ablation of the canker sore; and (d) starting the vibration to the distal section of the device to effect the vibrational massage therapy for the canker sore.

Figure 4:
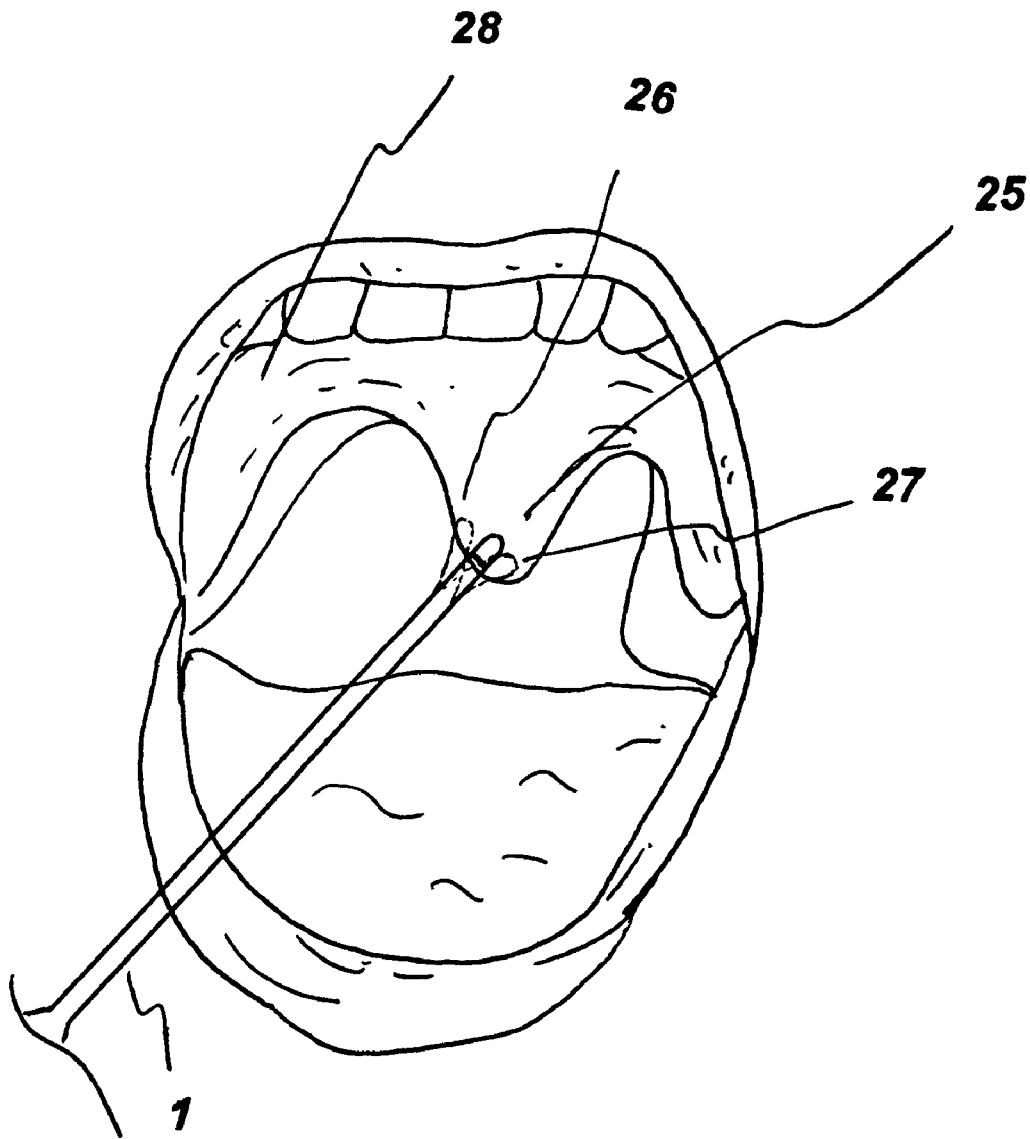
FIG. 4 shows a front view of the uvula being treated by the ablation device of the present invention.

FIG. 4 shows a front view of a patient's mouth 28, wherein the uvula 25 is treated according to the present method. After a patient's mouth is open, the ablation catheter is inserted into the mouth and the tip electrode 5 contacts the uvula. The tip electrode 5 vibrates between the points 26 and 27 of the cellular tissue of the uvula 25 to effect the vibrational massage therapy to the uvula while the RF energy is applied simultaneously to enhance the ablation efficiency.

An ablation treatment method for reducing the size and mass of cellular tissue of the uvula in order to reduce snoring comprises the steps of: (a) inserting an ablation device into the uvula of a patient, wherein the vibration device has a distal section, a distal end, a proximal end, at least a lumen extending therebetween, a handle, which has a cavity, attached at the proximal end of the device, and at least one opening at the distal section, wherein a tip electrode is disposed at the distal end, wherein the ablation device is leak-proof, except for the at least one opening at the distal section, and wherein the ablation device comprises means for generating vibration at the distal section, which is located within the handle; (b) contacting the electrode of the device against the cellular tissue of the uvula of the patient; (c) applying RF energy through a conducting wire to the tissue surrounding the exposed electrode area to effect ablation of the uvula tissue; and (d) starting the vibration to the distal section of the device to effect the vibrational massage therapy to the uvula tissue.

In a particular embodiment, the material for the electrode means of this invention consists of conductive metals such as platinum, iridium, gold, silver, stainless steel, Nitinol, or an alloy of these metals.

From the foregoing description, it should now be appreciated that an ablation catheter system for canker sores and uvula treatment, comprising a suitable energy source and a vibrational massage therapy, with an optional fluid irrigation capability has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A method of treating the canker sore of a patient, the method comprising:
    (a) inserting an ablation device into the mouth of a patient, wherein the ablation device has a distal section, a distal end, a proximal end, a lumen extending therebetween, a handle, which has a cavity, attached at the proximal end of the ablation device, and at least one opening at the distal section, wherein a tip electrode is disposed at the distal end, wherein the ablation device is leak-proof except for the at least one opening at the distal section, and wherein the ablation device comprises means for generating vibration at the distal section, which is located within the handle;
    (b) contacting the tip electrode of the ablation device against the canker sore of the patient;
    (c) applying RF energy to the tip electrode of the ablation device through a conducting wire to effect ablation of the canker sore; and
    (d) starting vibration to the distal section of the ablation device to effect the vibrational massage therapy to the canker sore.

2. The method of treating the canker sore of a patient as in claim 1, wherein the means for generating vibration at the distal section comprises a motor mounted in the cavity of the handle, which has a rotatable motor shaft, an elongated connecting shaft having a first end to which the electrode is connected, and a second end connected to the handle, a weight eccentrically mounted on the motor shaft with respect to the motor shaft axis, so as to rotate eccentrically, so that when the motor shaft rotates, the electrode vibrates.

3. The method of treating the canker sore of a patient as in claim 1, further comprising supplying a therapeutic agent through the at least one opening to the canker sore of the patient.

4. The method of treating the canker sore of a patient as in claim 3, wherein the therapeutic agent is selected from the group consisting of heparin solution, saline solution, fluoroquinolone, lactic acid, glycolic acid, alpha hydroxy organic acids, vitamins, povidone-iodine, nitrate compounds, virucidal agents, anti-ulcer agents, anti-inflammatory agents, antibiotics, and their mixtures.

5. An ablation treatment method for reducing size and mass of cellular tissue of an uvula in order to reduce snoring comprising the steps of:

(a) inserting an ablation device into the uvula of a patient, wherein the ablation device has a distal section, a distal end, a proximal end, a lumen extending therebetween, a handle, which has a cavity, attached at the proximal end of the ablation device, and at least one opening at the distal section, wherein a tip electrode is disposed at the distal end, wherein the ablation device is leak-proof except for the at least one opening at the distal section, and wherein the ablation device comprises means for generating vibration at the distal section, which is located within the handle;

(b) contacting the tip electrode of the ablation device against the cellular tissue of the uvula of the patient;

(c) applying RF energy to the tissue surrounding an exposed electrode area through a conducting wire to effect ablation of the cellular tissue; and (d) starting vibration to the distal section of the ablation device to effect the vibrational therapeutic massage for the cellular tissue of the uvula.

6. The ablation treatment method as in claim 5, wherein the means for generating vibration at the distal section comprises a motor mounted in the cavity of the handle, which has a rotatable motor shaft, an elongated connecting shaft, which has a first end, to which the electrode is connected, and a second end connected to the handle, a weight eccentrically mounted on the motor shaft with respect to the motor shaft axis, so as to rotate eccentrically, so that when the motor shaft rotates, the electrode vibrates.

7. The ablation treatment method as in claim 5 further comprising supplying a therapeutic agent to the cellular tissue of the uvula through the at least one opening.

8. The ablation treatment method as in claim 7, wherein the therapeutic agent is selected from the group consisting of heparin solution, saline solution, fluoroquinolone, lactic acid, glycolic acid, alpha hydroxy organic acids, vitamins, povidone-iodine, nitrate compounds, virucidal agents, anti-ulcer agents, anti-inflammatory agents, antibiotics, and their mixtures.

* * * * *